United States Patent [19]
Husemeyer et al.

[11] 3,973,900
[45] Aug. 10, 1976

[54] HAIR DYE
[75] Inventors: Hans Husemeyer; Eugene Konrad, both of Darmstadt, Germany
[73] Assignee: Wella AG, Darmstadt, Germany
[22] Filed: Sept. 9, 1974
[21] Appl. No.: 504,655

Related U.S. Application Data
[63] Continuation-in-part of Ser. No. 238,970, March 28, 1972, abandoned.

[30] Foreign Application Priority Data
Mar. 29, 1971 Switzerland.......................... 4530/71
Sept. 28, 1971 Switzerland....................... 14099/71

[52] U.S. Cl................................... 8/10.1; 8/10.2
[51] Int. Cl.² ............................................ A61K 7/13
[58] Field of Search ........................................ 8/10.1

[56] References Cited
UNITED STATES PATENTS

| | | | |
|---|---|---|---|
| 3,549,303 | 12/1970 | Kalopissis et al. | 8/10.1 |
| 3,563,684 | 2/1971 | Charle et al. | 8/10.1 |
| 3,591,638 | 7/1971 | Halasz | 8/10.1 |
| 3,617,164 | 11/1971 | Kalopissis et al. | 8/10.1 |
| 3,642,423 | 2/1972 | Bil et al. | 8/10.1 |

*Primary Examiner*—Dale R. Ore
*Attorney, Agent, or Firm*—Michael J. Striker

[57] ABSTRACT

Hair dyeing compositions containing a dye which has the formula

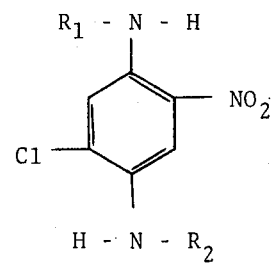

wherein $R_1$ and $R_2$ are each hydrogen or hydroxy ethyl alone or in conjunction with an oxidation and/or direct dyeing dye. The hair dyeing compositions can also include the conventional additives such as water soluble surface active agents, thickening agents, complex formers, antioxidants, softeners, perfumes, and the like.

13 Claims, No Drawings

HAIR DYE

CROSS-REFERENCE TO RELATED APPLICATION

This application is a continuation-in-part of application Ser. No. 238,970 filed Mar. 28, 1972, now abandoned.

BACKGROUND OF THE INVENTION

This invention relates to hair dyeing compositions containing aromatic nitro-amino benzene derivatives which are substituted by ring attached chlorine.

Nitro-amino benzene compounds such as 1-amino-2-nitro-4-aminobenzene or their N-substituted derivatives are known to be useful in dyeing human hair. These dyes are particularly useful where hair coloring in red shades is desired.

These dyes however have certain shortcomings and disadvantages which results in that the results with the dye compositions containing these red color dyes are unsatisfactory. This for example is manifested by the inadequate stability of the color shadings obtained therewith. Color shifts occur frequently, particularly caused by skin excretions such as acidic perspiration and as well by the action of sun on the dyed hair. The unsatisfactory stability of the color is also apparent when an additional acid rinsing of the hair is carried out following the dyeing treatment.

It is accordingly an object of the present invention to provide certain novel compositions which are useful in dyeing hair and which are not associated with the disadvantages of the known 1-amino-2-nitro-4-aminobenzene compound containing compositions.

Other and more detailed objects of this invention will be apparent from the following description and claims.

SUMMARY OF THE INVENTION

The dyeing compositions of this invention comprise as active dyeing ingredient a 1-amino-2-nitro-4-aminobenzene having the formula

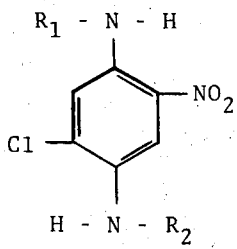

wherein $R_1$ and $R_2$ each represent hydrogen or hydroxy ethyl.

More particularly, the dyeing compositions herein comprise neutral or alkaline aqueous solutions of the above set out compounds. In addition to the water, alkalizing agent and dye, the compositions may contain an oxidation dye and/or a direct dyeing dye and can also contain the conventional ingredients found in dyeing compositions, such as organic solvents for the dye, thickeners, detergents, gums, antioxidants, softeners, perfumes and the like.

DETAILS OF THE INVENTION AND SPECIFIC EMBODIMENTS

The compositions of the invention give a wide spectrum of colors such as pure red to a bluish red and purple characterized by excellent stability and when used in combination with other dyes can easily produce other shades.

The 1-amino-2-nitro-4-aminobenzene compounds are made, as will be described further below, by well known processes. They can for example be prepared from chloro-p-phenylenediaminesulfate by acetylation, nitration and saponification or subsequent ethoxylation. Another process starts with 1,5-dichloro-4-aminobenzene and is carried out by nitration, acetylation, reaction with ethanol amine and subsequent saponification or further ethoxylation.

A preferred compound for use in accordance with the invention is one wherein $R_1$ is hydrogen and $R_2$ is hydrogen or hydroxyethyl ($—C_2H_4OH$). Hair dye compositions may be made using these 1-amino-2-nitro-5-chloro-4-aminobenzene compounds without addition of an oxidizing agent or with such agent.

The group of hair compositions which does not include oxidizing agents are those which in addition to the 1-amino-2-nitro-5-chloro-4-aminobenzene compound include direct dyes for the hair. Examples of suitable direct dyeing dyes are for instance other nitro dyes, azo dyes, anthraquinone dyes, etc. and are exemplified by the following groups of compounds:

Direct Dyes a. Aromatic nitro dyes
1,2-diamino-4-nitrobenzene
2-nitro-1,4-diaminobenzene
4-nitro-2-aminophenol
5-nitro-2-aminophenol
picramic acid-2,4-dinitro-6-aminophenol
b. Azo dyes
C.I. Acid Brown 4 (C.I. 14805)
C.I. Acid Orange 52 (C.I. 13025)
C.I. Acid Blue 135 (C.I. 13385)
c. Anthraquinone dyes
C.I. Disperse Violet 4 (C.I. 61105)
C.I. Disperse Blue 1 (C.I. 64500)
C.I. Disperse Red 15 (C.I. 60710)
C.I. Disperse Violet 1 (C.I. 61100)
1,4,5,8,tetraamino-anthraquinone
1,4-diaminoanthraquinone
d. Diamond Fuchsin (C.I. 42510)

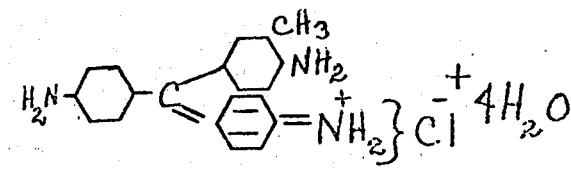

Leather Ruby HF (C.I. 42520)

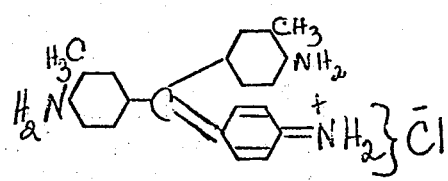

Diamond Green GX (C.I. 42040)

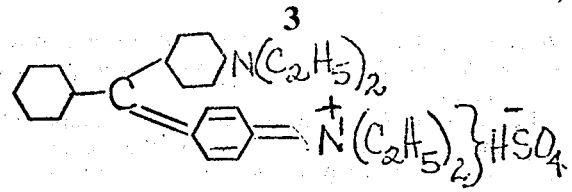

The oxidation dyes which may be present in the compositions of the invention include:
p-phenylenediamine
p-toluylenediamine
p-aminophenol
2,6-dimethyl-p-phenylenediamine In addition to the direct color forming dyes other related compounds are commonly included in dye compositions because they serve to modify or stabilize certain shades. These are commonly called modifiers and include the following:
meta-diamines
pyrocatechol
resorcinol
pyrogallol
alpha-naphthol and beta-naphthols
2,4-diamino-anisole
m-aminophenol
m-toluylenediamine When the 1-amino-2-nitro-5-chloro-4-aminobenzene dyestuff is used in combination with known dyes as set out above they can easily produce various blonde to brown shades. They lose little color upon shampooing, have good light fastness and rub fastness, they produce bright and lusterous shades and do not stain the scalp.

The dyeing compositions of this invention can be prepared by the conventional methods used in the hair dyeing art. Thus, they can be prepared by dissolving or dispersing the dye in water of the desired concentration. Water miscible organic solvents can be employed to facilitate solution of the dye; in this event, the dye can be dissolved first in the solvent and then diluted with water. Illustrative of the organic solvents which can be used, there can be mentioned: the lower alkyl monohydric alcohols, such as ethanol or ispropanol; lower aliphatic dihydric alcohols, e.g., propylene glycol; various polyhydric alcohols; ketones; and esters. The dispersion of the various ingredients can also be facilitated by addition of a detergent or dispersing agent, such as lauryl or myristyl sulfate or sulfonate. The water miscible organic solvents employed to facilitate solution of the dye can vary from about 1% to about 40% by weight of the composition, and preferably from about 2% to about 10%. The detergent or dispersing agent can vary from about 1% to about 30% by weight of the composition.

The dye compositions should have a concentration of the 1-amino-2-nitro-4-aminobenzene compound of the invention amounting to between about 0.01 and 1.0% by weight, preferably between 0.05 and 0.5% by weight. The total contents of dyes is within the range between about 0.01 and 3.0% by weight.

The pH of the dye compositions in accordance with the invention is in the range between 7 and 10.5, particularly between 7.5 and 9.5. Any selected compatible alkalizing agent should be used to give a pH of about 7 or 7.5 to about 10.5, and preferably a pH of about 7.5 or 8 to 9. The quantity of the alkalizing agent employed can vary over a wide range depending on the dye and particular alkalizing agent employed. Thus the alkalizing agent can vary from less than about 0.1% to about 5% and preferably from about 0.5% to about 2% by weight of the aqueous solution. The water content of the composition is ordinarily the major constituent and can vary over a wide range dependent in large measure on the quantity of other additives, such as solvents.

Any water soluble alkalizing agent that will not interfere (i.e., is compatible) with the dye employed, and will not precipitate the dye or introduce any possibility of toxicity under the conditions of use, or injure the scalp or hide of the pelt, at its ultimate concentration in the composition to be applied to the keratinous material, can be used. A preliminary test of some selected alkalizing agent can be made to note its compatibility with the dye or to introduce possibility of toxicity or injury.

Ammonium hydroxide, because of its freedom from toxicity over a wide concentration range and its economy is an acceptable alkalizing agent. However, there can be used in place of, or together with the ammonia, any other compatible ammonia derivative alkalizing agent, such as a lower alkanolamine, such as mono-, di- or triethanolamine, or alkylamines or alkylenediamines, such as monoethylamine, diethylamine, propylamine, dipropylamine or propylene diamine or a heterocyclic amine, such as morpholine. Any of these ammonia derivative alkalizing agents as well as ammonium hydroxide may be broadly referred to as an "ammonium alkalizant."

Also, as alkalizing agent, any alkaline earth hydroxide, for example, calcium hydroxide or magnesium hydroxide, can be used up to the limit of its water stability and at any concentration that fails to produce a precipitate with any of the components of the composition. The dissolved alkaline earth hydroxides, are preferred over the alkali metal hydroxides, such as sodium hydroxide, or potassium hydroxide, or carbonates, such as sodium carbonate and bicarbonate, any of which can also be used so long as their ultimate concentration in the final dyeing solution is below that which might possibly irritate the scalp.

The dye compositions which are used without oxidizing agents may of course additionally include cosmetic polymerisates which are employed to stabilize i.e., set and shape the hair at the time of dyeing.

The polymerisates conventionally used for this purpose include polyvinylpyrrolidone, polyvinylacetate, polyvinylalcohol or polyacrylic compounds such as acrylic acid or methacrylic acid polymerisates, basic polymerisates of esters of these two acids and amino alcohols or the salts or quaternary products of these basic polymerisates; furthermore, polyacrylonitrile, polyvinyllactams and copolymerisates of all of these different compounds such as polyvinylpyrrolidone-vinylacetate and similar copolymerisates.

As specific examples of these polymerisates, there may be mentioned the following:
polyvinylpyrrolidone having a molecular weight of 40,000 to 700,000
the copolymer of vinylpyrrolidone and vinylacetate (60:40) having a K value of 34 ∓ 6
polyacrylic acid diethylaminoethyl ester and polymethacrylic acid dimethylaminoethyl ester, the copolymer of polycrotonic acid and vinyl acetate.

The polymerisates usually are present in the dye composition in an amount between 1 and 4% by weight. The pH of the compositions containing the same is usually in the range between 6.0 and 9.0.

The application of compositions containing such additional setting lotions usually is completed by setting the hair to the desired style and subsequent drying.

The dyeing compositions of the invention can also contain conventional cosmetic additives such as conditioners, wetting agents, thickeners, softeners, perfume oils, etc.

A thickening agent can also be incorporated in the present dyeing composition which may be one or several of those commonly used in hair dyeing, such as hydroxyethyl cellulose ("Tylose"), sodium alginate or gum arabic, or cellulose derivatives, such as methyl cellulose, or the sodium salt of carboxymethyl cellulose, or acrylic polymers, such as polyacrylic acid sodium salt, or inorganic thickeners, such as bentonite. The quantity of thickening agent can vary over a wide range, such as that of from about 0.1% to 20% and preferably from about 0.5% to 5% by weight.

The compounds of the invention can furthermore as noted above be used in combinations where an additional dye is used which requires an oxidizing agent. Examples of these dyes which require an oxidative development have been given previously.

The dye compositions which contain oxidative dyes should contain the 1-amino-2-nitro-4-aminobenzene compounds in a concentration of between about 0.01 and 1.0 by weight, preferably between 0.05 and 0.5% by weight. The total contents of dyestuff in these compositions should be between about 0.1 and 5.0% by weight.

As oxidizing agent for developing the oxidative hair dye preferably hydrogen peroxide or addition compounds thereof are used. The consistency of these dye compositions is preferably that of a cream or a gel.

These dye compositions containing oxidative dyes can of course also contain the conventional cosmetic additives such as for instance the antioxidants, complexing agents, thickening agents, surface active agents, conditioners, perfuming oils, etc.

Water soluble surface active agents can also be utilized in formulating dyeing compositions of this invention. These can be anionic, nonionic or cationic. The quantity of these materials contained in the composition can vary widely. Generally, however, it will constitute from about 0.25% to 15% by weight of the composition and preferably from about 0.25% to 10% by weight of the composition.

As examples of suitable surface active agents there may be mentioned higher alkylbenzene sulfonates, alkylnaphthalene sulfonates, sulfonated esters of alcohols and polybasic acids, taurates, fatty alcohol sulfates, sulfates of branched chain or secondary alcohols, alkyldimethylbenzylammonium chloride, polyoxyethylene alkyl ether, alkylphenoxypolyoxyethylene-ethanol and more specifically lauryl sulfate, polyoxyethylene lauryl ester, myristyl sulfate, glycerinmonostearate, sodium salt of palmitoylmethyltaurine, lauryl sulfonate, myristyl sulfonate, lauric acid diethanolamide, polyoxyethylene stearate, stearyldimethylbenzylammonium chloride, dodecylbenzene sodium sulfonate, nonylnaphthalene sodium sulfonate, dioctyl sodium sulfosuccinate, sodium-n-methyl-n-oleoyltaurate, oleic acid ester of sodium isothionate, sodium dodecyl sulfate, sodium salt of 3,9-diethyltlidecanol-6-sulfate and others.

Conditioning agents such as water soluble lanolin, lauric acid diethanolamide and cetylpyridinium chloride can also be present.

As softeners, glycerin, diethylphthalate and citric acid triethyl ester may be advantageously employed.

The conventional antioxidants may be employed. These include sodium sulfite, ascorbic acid and the salts thereof.

Additionally, complex forming or chelating agents may be present such as the disodium salt of ethylene diamine tetraacetic acid and nitrilotriacetic acid.

Finally, perfuming agents may be included such as lavendar oil, rosewater and the like.

The reaction time or time of contact of the dyeing composition with the hair is not critical and can vary over a wide range used in the hair dyeing art, such as periods of about 5 minutes to about 2 hours, and preferably from about 15 minutes to about 60 minutes. The dyeing temperature can vary over wide limits as is conventional in the art. Thus, the dyeing temperature can vary from about room temperature e.g., about 20°C. to above about 60°C., and preferably from about 20°C. to about 45°C.

The following examples are further illustrative of the present invention. It should be understood, however, that the invention is not limited thereto.

EXAMPLE 1

In this example a dye composition was prepared having the following composition:

| | |
|---|---|
| 0.5 g | hydroxyethylcellulose ("Tylose") |
| 5.0 g | laurylalcohol diglycolethersulfate (28% aqueous solution) |
| 15.0 g | isopropylalcohol |
| 0.1 g | 1,4-diamino-2-nitro-5-chlorobenzene |
| 0.03 g | ammonia (25%) |
| 79.37 g | water |
| 100.00 g | |

This composition was applied to white human hair and permitted to act thereon for about 10 minutes. After rinsing with water and drying, the hair will have a bright red color.

EXAMPLE 2

A dye composition having the following composition was prepared:

| | |
|---|---|
| 2.00 g | polyvinylpyrrolidone |
| 0.10 g | glycerin |
| 40.00 g | isopropylalcohol |
| 0.15 g | 1,4-diamino-2-nitro-5-chlorobenzene |
| 57.75 g | water |
| 100.00 g | |

White human hair was first treated with the above composition, then set to the desired hair style and dried. The hair has a bright red color and a definitely set shape.

EXAMPLE 3

A dye composition having the following composition was prepared:

| | |
|---|---|
| 35.0 g | oleic acid |
| 15.0 g | isopropylalcohol |
| 18.0 g | ammonia (25%) |
| 0.2 g | disodium salt of ethylenediamine tetraacetic acid |
| 0.1 g | sodium sulfite |
| 0.8 g | p-toluylenediaminesulfate |
| 0.2 g | resorcinol |
| 0.05 g | m-aminophenol |
| 0.2 g | 1-amino-2-nitro-4-beta-hydroxyethylamino-5-chlorobenzene |

-continued

| | |
|---|---|
| 30.45 g | water |
| 100.00 g | |

50 ml of this composition were mixed shortly before application with 50 ml of hydrogen peroxide (6%). The resulting gel was then applied to grey human hair and allowed to act for 30 minutes. The hair was then rinsed with water and dried. The hair had a reddish-blonde color.

EXAMPLE 4

The following composition was prepared:

| | |
|---|---|
| 2.0 g | copolymerisate of vinylpyrrolidone-vinylacetate 60:40 |
| 0.1 g | glycerin |
| 40.0 g | isopropylalcohol |
| 0.15 g | 1-amino-2-nitro-4-beta-hydroxyethylamino-5-chlorobenzene |
| 57.75 g | water |
| 100.00 g | |

White human hair was treated with the above composition, set to the desired style and then dried. The hair had a bluish-red color and was set in the desired style.

EXAMPLE 5

A liquid hair dyeing composition of the following components was prepared:

| | |
|---|---|
| 5.0 g | laurylalcohol diglycolethersulfate (28% aqueous solution) |
| 0.5 g | hydroxyethylcellulose ("Tylose") |
| 15.0 g | ethylalcohol |
| 0.1 g | 1-amino-2-nitro-4-beta-hydroxyethylamino-5-chlorobenzene |
| 0.03 g | ammonia (25%) |
| 79.37 g | water |
| 100.00 g | |

This composition was applied to white human hair and permitted to act on the hair for 10 minutes. The hair was then rinsed with water and finally dried. The hair had a bluish-red color.

EXAMPLE 6

A liquid hair dye composition as follows was prepared:

| | |
|---|---|
| 0.5 g | hydroxyethylcellulose ("Tylose") |
| 5.0 g | laurylalcohol diglycolethersulfate (28% aqueous solution) |
| 15.0 g | isopropylalcohol |
| 0.1 g | 1,4-diamino-2-nitro-5-chlorobenzene |
| 0.3 g | Acid Brown 4 (C.I. 14 805) |
| 0.03 g | ammonia (25%) |
| 79.07 g | water |
| 100.00 g | |

This composition was applied to white human hair and permitted to act on the hair for 10 minutes. After rinsing with water and drying, the hair had a reddish-brown color.

EXAMPLE 7

A liquid hair dye having the following composition was prepared:

| | |
|---|---|
| 0.5 g | hydroxyethylcellulose ("Tylose") |
| 5.0 g | laurylalcohol diglycolethersulfate (28% aqueous solution) |
| 15.0 g | isopropylalcohol |
| 0.1 g | 1-beta-hydroxyethylamino-2-nitro-4-amino-5-chlorobenzene |
| 0.03 g | ammonia (25%) |
| 79.37 g | water |
| 100.00 g | |

This composition was applied to white human hair and permitted to act for 10 minutes. After rinsing with water and drying the hair had a purple color.

EXAMPLE 8

A hair dyeing composition as follows was prepared:

| | |
|---|---|
| 2.00 g | polyvinylpyrrolidone |
| 0.10 g | glycerin |
| 40.00 g | isopropylalcohol |
| 0.15 g | 1-beta-hydroxyethylamino-2-nitro-4-amino-5-chlorobenzene |
| 57.75 g | water |
| 100.00 g | |

White human hair was first treated with the dyeing composition, set to the desired style and is then subjected to drying. The hair had a purple color and was set as desired.

EXAMPLE 9

The following dye composition was prepared:

| | |
|---|---|
| 35.0 g | oleic acid |
| 15.0 g | isopropylalcohol |
| 18.0 g | ammonia (25%) |
| 0.2 g | disodium salt of ethylenediamine tetraacetic acid |
| 0.1 g | sodium sulfite |
| 0.8 g | toluylenediamine sulfate |
| 0.2 g | resorcinol |
| 0.05 g | m-aminophenol |
| 0.2 g | 1,4-di-(beta-hydroxylethylamino)-2-nitro-5-chlorobenzene |
| 30.45 g | water |
| 100.00 g | |

50 ml of this hair dyeing composition were mixed shortly prior to application with 50 ml of hydrogen peroxide (6%). The gel thusly formed was then applied to grey human hair and permitted to act thereon for 30 minutes. The hair was then rinsed with water and dried. The hair had a reddish-blonde color.

The same dye composition was prepared but with 0.3 g lavendar perfume and 2.0 g lauric acid diethanolamide. At the same time the water content was reduced to 28.15 g.

The same results were achieved with this composition.

EXAMPLE 10

| | |
|---|---|
| 2.0 g | copolymerisate of vinylpyrrolidone-vinylacetate 60:40 |
| 0.1 g | glycerin |
| 40.0 g | isopropyl alcohol |
| 0.15 g | 1,4-di-(beta-hydroxyethylamino)-2-nitro-5-chlorobenzene |
| 57.75 g | water |
| 100.00 g | |

The above composition was applied to white human hair and the hair set to the desired style and then dried. The color of the hair was violet-red and was set in the desired style.

EXAMPLE 11

A liquid hair dyeing composition as follows was prepared:

| | |
|---|---|
| 5.0 g | lauryl alcohol diglycolethersulfate (28% aqueous solution) |
| 0.5 g | hydroxyethylcellulose ("Tylose") |
| 15.0 g | ethyl alcohol |
| 0.1 g | 1,4-di-(beta-hydroxyethylamino)-2-nitro-5-chlorobenzene |
| 0.03 g | ammonia (25%) |
| 79.37 g | water |
| 100.00 g | |

The composition was applied to white human hair and permitted to act thereon for ten minutes. The hair was then rinsed with water and dried. The hair had a violet-red color.

EXAMPLE 12

A hair dye having the following composition was prepared:

| | |
|---|---|
| 0.5 g | hydroxyethylcellulose ("Tylose") |
| 5.0 g | lauryl alcohol diglycolethersulfate (28% aqueous solution) |
| 15.0 g | isopropyl alcohol |
| 0.1 g | 1-beta-hydroxyethylamino-2-nitro-4-amino-5-chlorobenzene |
| 0.3 g | Acid Brown 4 (C.I. 14 805) |
| 0.03 g | ammonia (25%) |
| 79.07 g | water |
| 100.00 g | |

The composition was applied to white human hair and permitted to act thereon for ten minutes. After rinsing with water and drying, the hair had a reddish-brown color.

EXAMPLE 13

1,4-Diamino-2-Nitro-5-Chlorobenzene a. 1000 g of chloro-p-phenylenediaminesulfate were dissolved in water and the base was set free by means of ammonia. The precipitated base was then removed by suction and dried. The yield amounted to 600 g (chloro-p-phenylenediamine).

600 g of the free base were then heated with 500 ml acetic acid and 1 kg of acetic acid anhydride for 1 hour to a temperature of 140°C. The solution was then poured onto ice and the acetyl compound thusly precipitated. It was removed by suction and dried. Yield: 645.5 g of chloro-1,4-bis-acetaminobenzene; m.p.: 202°–203°C.

b. 224.5 g (1 mole) of chloro-1,4-bis-acetaminobenzene were dissolved in 1000 ml of concentrated sulfuric acid at −15°C. The solution was then nitrated at −5°C. with a mixture of 400 ml sulfuric acid (1.84) and 40 ml $HNO_3$ (d+1.5). The solution was then stirred for 1 hour and finally poured onto ice. The precipitated acetyl compound was removed by suction and thoroughly washed with water. The still wet acetyl compound was then saponified with 1 l hydrochloric acid (half concentrated) and it was then cooled and reacted with ammonia. Yield: 137 g of 1,4-diamino-2-nitro-5-chlorobenzene; m.p.: 157°C. Analysis: $C_6H_6ClO_2N_3$

| | C | H | N |
|---|---|---|---|
| Theoretical | 38.42 | 3.23 | 22.40 |
| Found | 38.54 | 3.21 | 22.32 |
| | 38.32 | 3.24 | 22.46 |

EXAMPLE 14

1-Amino-2-Nitro-4-Beta-Hydroxyethylamino-5-Chlorobenzene 18.7 g (0.1 mole) of 1,4-diamino-2-nitro-5-chlorobenzene were dissolved in 20 ml methylglycol and 12 g ethylenechlorohydrin (1.5 mole) and the solution then heated on a bath having a temperature of 120°C. 6.6 g of sodium hydroxide dissolved in 60 ml water were then slowly added dropwise over a period of 3 hours. Heating was then continued for 1 hour whereupon a chromatographic check wss made to ascertain whether most or all of the starting compound had been reacted. After cooling the mass was diluted with water and the precipitated hydroxyethylated compound was removed by suction. Recrystallation was effected from water and thereafter from a 20% acetic acid. Yield: 4.5 g; m.p.: 130°–131°C. Analysis: $C_8H_{10}ClO_3N_3$

| | C | H | N |
|---|---|---|---|
| Theoretical | 41.48 | 4.35 | 18.14 |
| | 41.74 | 4.37 | 18.23 |
| | 41.36 | 4.31 | 18.23 |

EXAMPLE 15

1-Beta-Hydroxyethylamino-2-Nitro-4-Amino-5-Chlorobenzene a. 648 g (4 mole) of 1,5-dichloro-4-aminobenzene were dissolved at −10°C. in 3200 ml of concentrated $H_2SO_4$. Nitration was then effected with a mixture of 1600 ml of concentrated $H_2SO_4$ and 160 ml $NHO_3$ (d=1.5) at about 0°C. After this step was completed, the mass was permitted to react for about 1 hour. The mixture was then poured onto 16 l ice water. The precipitated nitro compound was removed with suction and recrystallized from isopropanol/water. Yield: 455 g 2-nitro-4-amino-1,5-dichlorobenzene; m.p.: 103°–104°C.

b. 455 g (2.2 mole) of 2-nitro-4-amino-1,5-dichlorobenzene were dissolved in 1 l of $CH_3COOOH$ and acetylated at an elevated temperature with 300 ml acetic acid anhydride. After cooling, the solution was poured onto 10 l of ice water. The precipitated acetyl compound was removed with suction, washed and dried. Yield: 500 g of 2-nitro-4-acetylamino-1,5-dichlorobenzene; m.p.: 128°–130°C.

c. 500 g (2 mole) of 2-nitro-4-acetylamino-1,5-dichlorobenzene were dissolved in 1900 ml methylglycol. 246 g of ethanolamine were added dropwise at a bath temperature of 140°C. Heating was then continued for another hour while stirring. After cooling the solution was poured onto 12 l of water. The precipitated product was removed by suction and washed with water; m.p.: 183°–185°C.

The still wet acetyl compound was saponified with 2000 ml of an alcoholic solution of hydrogen chloride (1:1). The thus formed hydrochloride was removed by suction and washed with cold alcohol.

The resulting compound was then dissolved in water and the base was recovered by adding ammonia. After removal by suction and drying, recrystallization was effected from acetic acid ethyl ester. Yield: 113 g of 1-beta-hydroxyethylamino-2-nitro-4-amino-5-chlorobenzene; m.p.: 149°C. Analysis: $C_8H_{10}N_3O_3Cl$

|  | C | H | N |
|---|---|---|---|
| Theoretical | 41.48 | 4.35 | 18.44 |
| Found | 41.51 | 4.50 | 18.60 |

EXAMPLE 16
1,4-Di-(Beta-Hydroxyethylamino)-2-Nitro-5-Chlorobenzene 79.0 g (0.33 mole) of 1-beta-hydroxyethylamino-2-nitro-4-amino-5-chlorobenzene were dissolved in 150 ml methylglycol and 36 g (0.5 mole) ethylenechlorohydrin. 19.8 g of NaOH dissolved in 180 ml water were then added while stirring over a period of 3 hours at a bath temperature of 130°C. The final product was removed by suction after cooling and was recrystallized from water. Yield: 35 g 1,4-di-(beta-hydroxyethylamino)-2-nitro-5-chlorobenzene; m.p.: 127°–128°C. Analysis: $C_{10}H_{14}N_3O_4Cl$

|  | C | H | N |
|---|---|---|---|
| Theoretical | 43.56 | 5.13 | 15.24 |
| Found | 43.31 | 5.20 | 15.40 |

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

What is claimed is:

1. A hair dyeing composition consisting essentially of an aqueous solution containing between 0.01 and 1.0% by weight of a dye having the formula

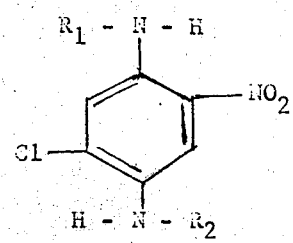

wherein $R_1$ and $R_2$ are hydrogen or hydroxyethyl substituents, the said composition having a pH of from between 7.0 to and about 10.5.

2. A hair dyeing composition as defined in claim 1 in which said dye is present in an amount between 0.05 and 0.5% by weight of the composition.

3. A hair dyeing composition according to claim 1 wherein said dye $R_1$ is hydrogen and $R_2$ is hydrogen or hydroxyethyl.

4. A hair dyeing composition according to claim 1 additionally containing at least one oxidation or direct dye.

5. A hair dyeing composition according to claim 4 wherein said direct dye is a nitro dye, azo dye, anthraquinone dye, Diamond Fuchsin

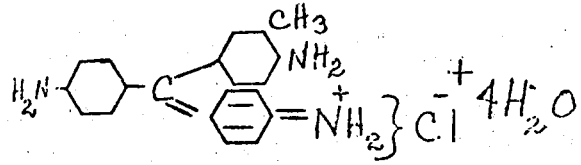

, Leather Ruby HF

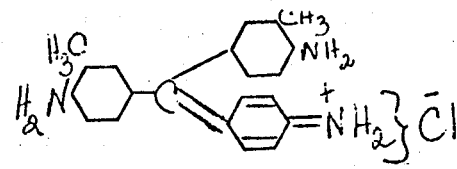

or Diamond Green GX

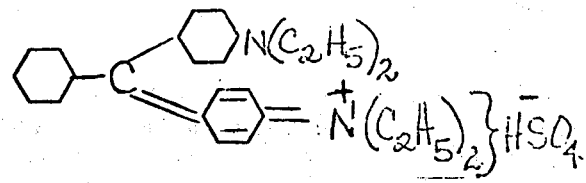

6. A hair dyeing composition according to claim 4 wherein said oxidative dye is p-phenylenediamine, p-toluylenediamine, p-aminophenol, or 2,6-dimethyl-p-phenylenediamine.

7. A hair dyeing composition according to claim 4 wherein the total content of dyes is within the range of 0.01 and 3.0% by weight.

8. A hair dyeing composition according to claim 1 additionally containing at least one member of the group consisting of alkalizing agent, surface active agent, thickening agent, chelating agent, antioxidant, softener, perfume, and organic solvent.

9. A hair dyeing composition according to claim 8 wherein said solvent is present in an amount of from about 1 to 40% by weight of the composition.

10. A hair dyeing composition according to claim 8 wherein said surface active agent is present in an amount of from about 0.25 to 10% by weight of the composition.

11. A hair dyeing composition according to claim 8 wherein said alkalizing agent is present in an amount of from about 0.1 to about 5% by weight of the composition.

12. A hair dyeing composition according to claim 8 wherein said thickening agent is present in an amount of from about 0.1 to 20% by weight of the composition.

13. A process for dyeing hair which comprises applying thereto a tinctorially effective quantity of a composition according to claim 1.

* * * * *